(12) United States Patent
Gundlach et al.

(10) Patent No.: US 12,208,200 B2
(45) Date of Patent: Jan. 28, 2025

(54) STEAM INHALER

(71) Applicant: Helen of Troy Limited, St. Michael (BB)

(72) Inventors: John D. Gundlach, North Hampton, NH (US); Kevin M. Johnson, Natick, MA (US); Dio Climaco Cavero, Merrick, NY (US)

(73) Assignee: HELEN OF TROY LIMITED, St. Michael (BB)

( * ) Notice: Subject to any disclaimer, the term of this patent is extended or adjusted under 35 U.S.C. 154(b) by 797 days.

(21) Appl. No.: 17/483,875

(22) Filed: Sep. 24, 2021

(65) Prior Publication Data
US 2023/0095052 A1  Mar. 30, 2023

(51) Int. Cl.
| | | |
|---|---|---|
| *A61M 15/00* | (2006.01) | |
| *A61H 33/12* | (2006.01) | |
| *H05B 1/02* | (2006.01) | |

(52) U.S. Cl.
CPC ......... *A61M 15/0001* (2014.02); *A61H 33/12* (2013.01); *A61M 2205/3653* (2013.01); *A61M 2205/75* (2013.01); *H05B 1/025* (2013.01)

(58) Field of Classification Search
CPC ...... A61M 15/0001; A61M 2205/3653; A61M 2205/75; A61M 15/0015; A61M 16/0808;
(Continued)

(56) References Cited

U.S. PATENT DOCUMENTS

| 4,319,566 A | * | 3/1982 | Hayward | ............. | A61M 11/042 |
| | | | | | 128/203.26 |
| 4,399,349 A | * | 8/1983 | Deming | ............... | A61M 11/042 |
| | | | | | 4/537 |

(Continued)

FOREIGN PATENT DOCUMENTS

| CN | 101325979 B | * | 8/2013 | ............... | A61B 5/01 |
| CN | 109602977 | | 4/2019 | | |

(Continued)

OTHER PUBLICATIONS

Machine Translation of CN101325979B; Accessed Sep. 12, 2024 (Year: 2024).*

(Continued)

*Primary Examiner* — Kendra D Carter
*Assistant Examiner* — Alexander J Guerrero
(74) *Attorney, Agent, or Firm* — RANKIN, HILL & CLARK LLP

(57) ABSTRACT

A steam inhaler includes a steam chamber housing having mounted therein a heater assembly. The steam chamber housing defines a steam chamber adapted to receive water. A fitting mounted to the steam chamber housing has a steam conduit section extended toward an exterior vent opening, a nozzle conduit section extended from the steam conduit, and a fresh air conduit section extended from the steam conduit section at a location downstream of the nozzle conduit section. The fitting is configured such that steam flows freely from the steam chamber, through the steam conduit section toward the exterior vent opening, a suction provided at the nozzle redirects at least a portion of the steam into the nozzle conduit section toward a mask, and the fresh air conduit directs fresh air into the steam conduit section to reduce a temperature of the steam exiting the exterior vent opening.

19 Claims, 10 Drawing Sheets

US 12,208,200 B2
Page 2

(58) Field of Classification Search
CPC .......... A61M 2205/121; A61M 11/042; A61M 15/08; A61M 16/0066; A61M 2205/07; A61M 2205/123; A61M 2205/125; A61M 2205/21; A61M 2205/276; A61M 2205/3368; A61M 2205/3606; A61M 2205/362; A61M 2205/7545; A61M 2205/8206; A61M 2205/8262; A61M 16/06; A61M 2202/0468; A61M 2205/8237; A61M 16/16–168; A61H 33/12; H05B 1/025; A24F 1/22
See application file for complete search history.

(56) References Cited

U.S. PATENT DOCUMENTS

| | | |
|---|---|---|
| 4,616,122 A | 10/1986 | Burian |
| 4,903,850 A | 2/1990 | Frank et al. |
| 6,842,918 B2 | 1/2005 | Fung |
| 6,904,624 B2 | 6/2005 | Leung |
| 7,500,479 B2 | 3/2009 | Nichols |
| D685,896 S | 7/2013 | Niedermann |
| 9,702,575 B2 | 7/2017 | Niedermann |
| 9,845,962 B2 | 12/2017 | Niedermann |
| D835,763 S | 12/2018 | Niedermann |
| D886,268 S | 6/2020 | Montagnino |
| 10,729,871 B2 | 8/2020 | Niedermann |
| 10,845,072 B2 | 11/2020 | Montagnino |
| D904,592 S | 12/2020 | Niedermann |
| D919,070 S | 5/2021 | Niedermann |
| 2007/0075448 A1 | 4/2007 | Niedermann |
| 2011/0009048 A1 | 1/2011 | Niedermann |
| 2016/0313016 A1 | 10/2016 | Niedermann |
| 2018/0078729 A1 | 3/2018 | Niedermann |
| 2019/0350334 A1 | 11/2019 | Montagnino |
| 2019/0350335 A1 | 11/2019 | Montagnino |
| 2019/0351155 A1 | 11/2019 | Montagnino |
| 2019/0353362 A1* | 11/2019 | Montagnino ........... F24F 8/108 |
| 2021/0128866 A1 | 5/2021 | Higashiyama |

FOREIGN PATENT DOCUMENTS

| | | | |
|---|---|---|---|
| CN | 209422678 | 9/2019 | |
| DE | 8322139 | 11/1983 | |
| GB | 2487401 | 7/2012 | |
| GB | 2487401 A * | 7/2012 | ........... A61H 33/065 |

OTHER PUBLICATIONS

International Search Report/Written Opinion issued in PCT/US22/45354 issued Jan. 31, 2023.

* cited by examiner

STEAM INHALER

BACKGROUND

A variety of inhaling devices are available in the market. One kind of inhaler, i.e., a steam inhaler is generally available as a table top inhaler or a hand-held inhaler. Currently, available methods employed by these devices direct all steam generated in a steam chamber into a mask via a single, continuous conduit. This can create a sense of burning on the skin of the face when a user is not inhaling, and to avoid this, the design temperatures are typically lowered. Current methods to achieve this result add inlet holes in the steam conduit and/or mask to draw in ambient air to reduce the steam temperatures. This technique can reduce the effectiveness of the steam, since the nose and mouth can typically benefit from and withstand much higher temperatures than would be comfortable for sensitive areas of the skin around the nose and mouth. Invariably, this means the temperature is still too hot for some and too cold for others. Current steam inhalers are also not designed for use at any angle, and can be difficult to clean, frequently as a result of mineral deposits that result from the evaporation of the water during steam generation.

SUMMARY

According to one aspect, a steam inhaler comprises a steam chamber housing having mounted therein a heater assembly. The steam chamber housing defines a steam chamber directly above the heater assembly, the steam chamber adapted to receive water. A fitting is mounted to the steam chamber housing. The fitting has a steam conduit section extended from the steam chamber to an exterior vent opening, a nozzle conduit section extended from the steam conduit section at a location downstream of the steam chamber, and a fresh air conduit section extended from the steam conduit section at a location downstream of the nozzle conduit section. A steam nozzle in communication with the nozzle conduit section directs steam into a mask releasably fitted onto the steam nozzle. The fitting is configured such that steam flows freely from the steam chamber, through the steam conduit section toward the exterior vent opening, and a suction provided at the nozzle redirects at least a portion of the steam into the nozzle conduit section, and the fresh air conduit directs fresh air into the steam conduit section to reduce a temperature of the steam exiting the exterior vent opening.

According to another aspect, a steam inhaler comprises a lower housing assembly and an upper housing assembly. The lower housing assembly includes a lower steam chamber housing having mounted therein a heater assembly. The lower steam chamber housing defines a lower steam chamber directly above the heater assembly. The upper housing assembly includes an upper steam chamber housing releasably mounted to the lower steam chamber housing, the connection of the upper steam housing to the lower steam housing allowing for the removal of the upper housing assembly from the lower housing assembly. A fitting is mounted to the upper steam chamber housing. The fitting has a steam conduit section in communication with the lower steam chamber and an exterior vent opening, a nozzle conduit section extended from the steam conduit section and in communication with a steam nozzle, and a fresh air conduit section extended from the steam conduit section at a location downstream of the nozzle conduit section and in communication with an interior of the lower housing assembly. A mask is releasably fitted onto the steam nozzle. The fitting is configured such that steam flows freely from the lower steam chamber straight through the steam conduit section toward the exterior vent opening, and a suction provided at the nozzle redirects the steam into the nozzle conduit section, and the fresh air conduit directs fresh air into the steam conduit section to reduce a temperature of the steam exiting the exterior vent opening. A water reservoir is removably mounted to the lower housing assembly. The water reservoir has a filter for filtering water to be delivered to the lower steam chamber.

DETAILED DESCRIPTION

It should, of course, be understood that the description and drawings herein are merely illustrative and that various modifications and changes can be made in the structures disclosed without departing from the present disclosure. Spatially relative terms, such as "lower," "upper" and the like may be used to describe an element and/or feature's relationship to another element(s) and/or feature(s) as, for example, illustrated in the figures. It will be understood that the spatially relative terms are intended to encompass different orientations of the exemplary steam inhaler in use and/or operation in addition to the orientation depicted in the figures. Further, the term "substantially" is defined to be essentially conforming to the particular dimension, shape or other word that substantially modifies, such that the component need not be exact.

Figure 1:
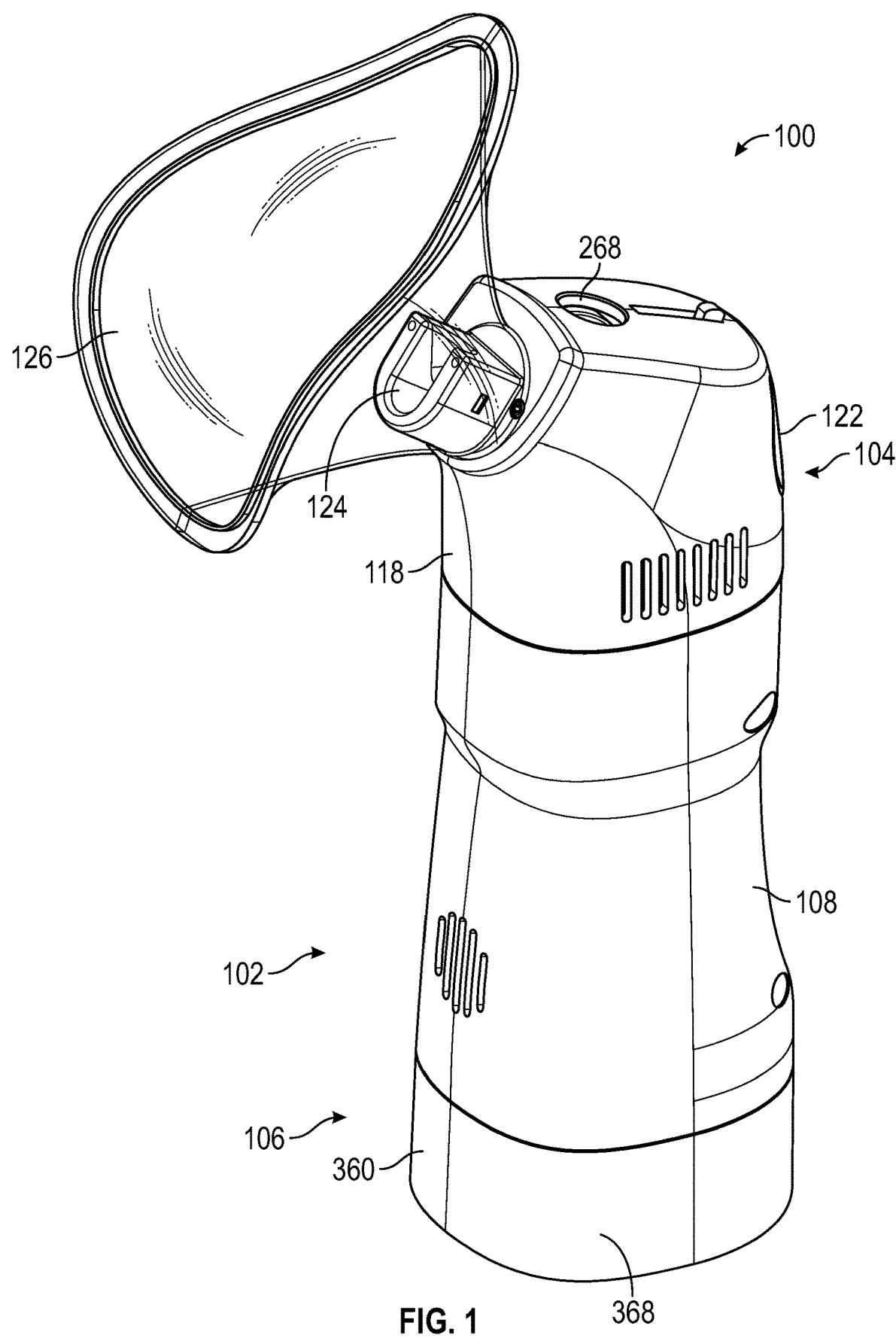
FIG. 1 is a perspective view of a steam inhaler according to the present disclosure, the steam inhaler including a lower housing assembly, an upper housing assembly removably mounted to the lower housing assembly, and a water reservoir removably mounted to the lower housing assembly.
Figure 2:
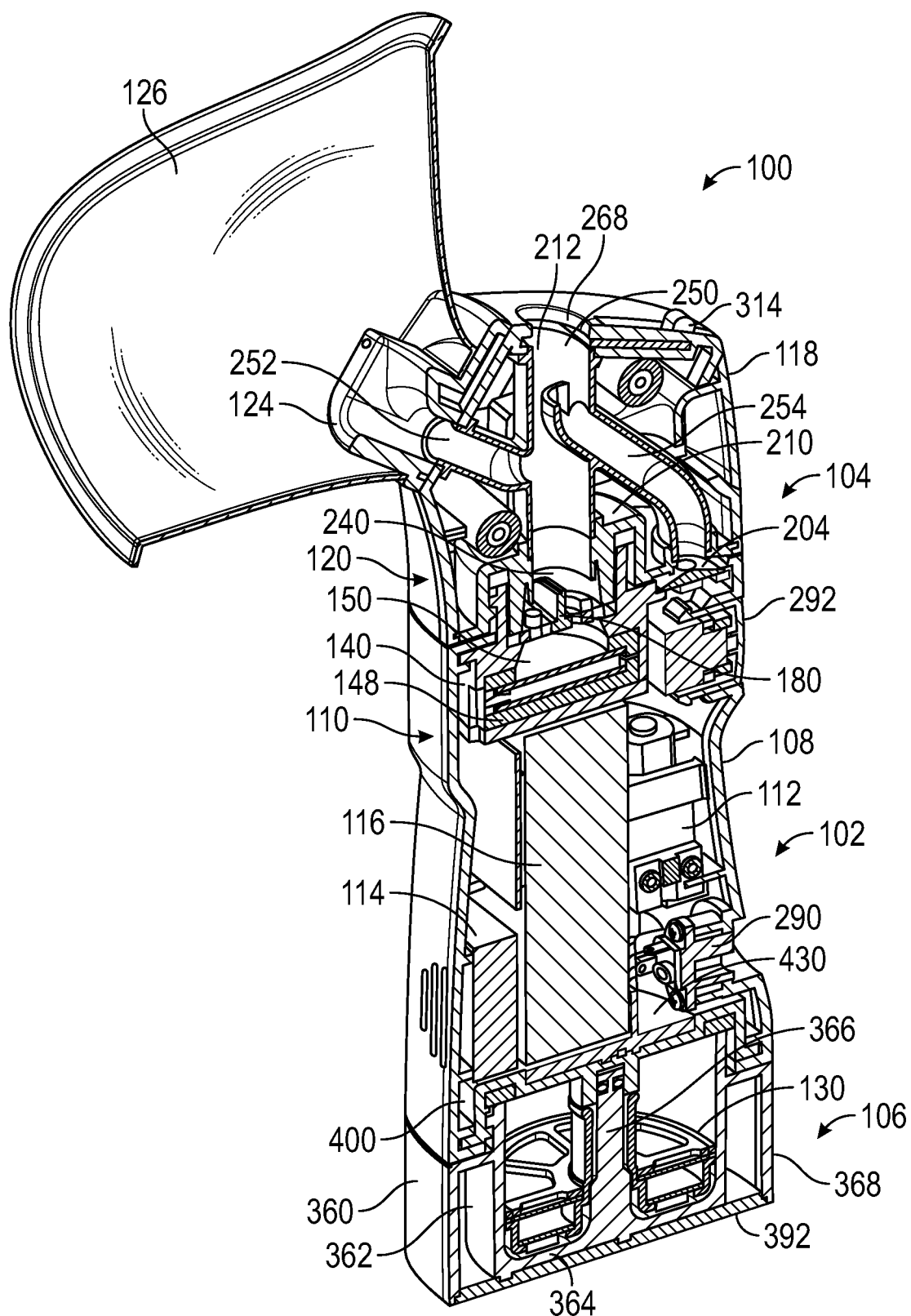
FIG. 2 is a cross-sectional view of FIG. 1.

Referring now to the drawings, wherein like numerals refer to like parts throughout the several views, FIGS. 1 and 2 illustrate an exemplary steam inhaler 100 according to the present disclosure, the steam inhaler configured to heat a liquid, such as water, to generate steam, and control the direction of steam flow to the area of a user's nose and mouth. The steam inhaler 100 generally comprises a lower housing assembly 102, an upper housing assembly 104 removably mounted to the lower housing assembly 102, and a water reservoir 106 removably mounted to the lower housing assembly 102. As will be described in detail below, the lower housing assembly 102 includes a housing 108 for housing a lower steam assembly 110, a means for generating water pressure such as a pump 112 (for example, a peristaltic pump or an air pump), a blower 114, and a power source 116.

The upper housing assembly 104 includes a housing 118 for housing an upper steam assembly 120 and an extendable scented pad receptacle or drawer 122, and further includes a steam nozzle 124 and a mask 126 releasably fitted onto the steam nozzle. The removable water reservoir 106 includes a filter 130 mounted within the water reservoir for filtering water to be delivered to the lower steam assembly 110 via the pump 112.

Figure 3:
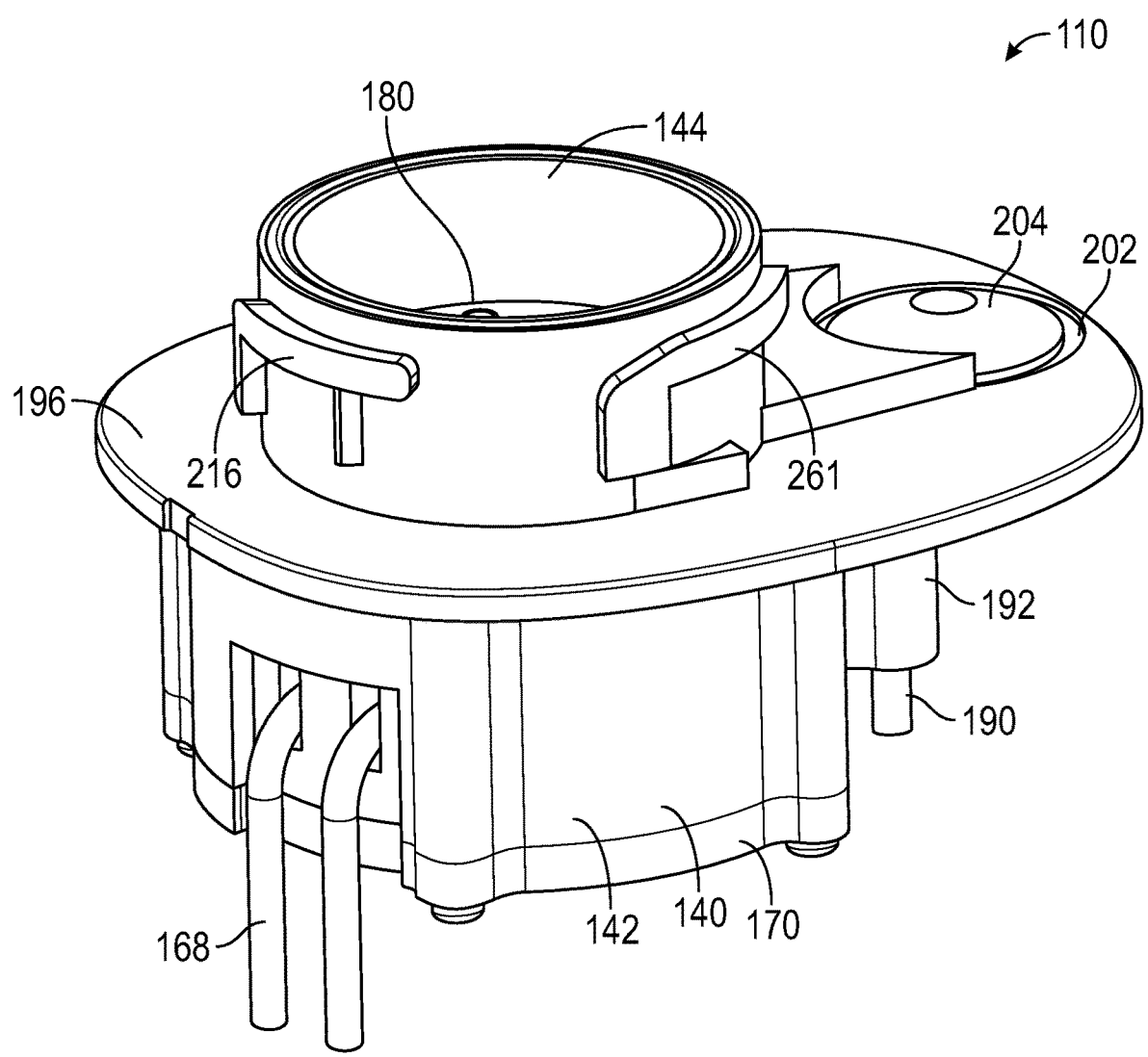
FIG. 3 is a perspective view of a lower steam chamber assembly of the lower housing assembly.
Figure 4:
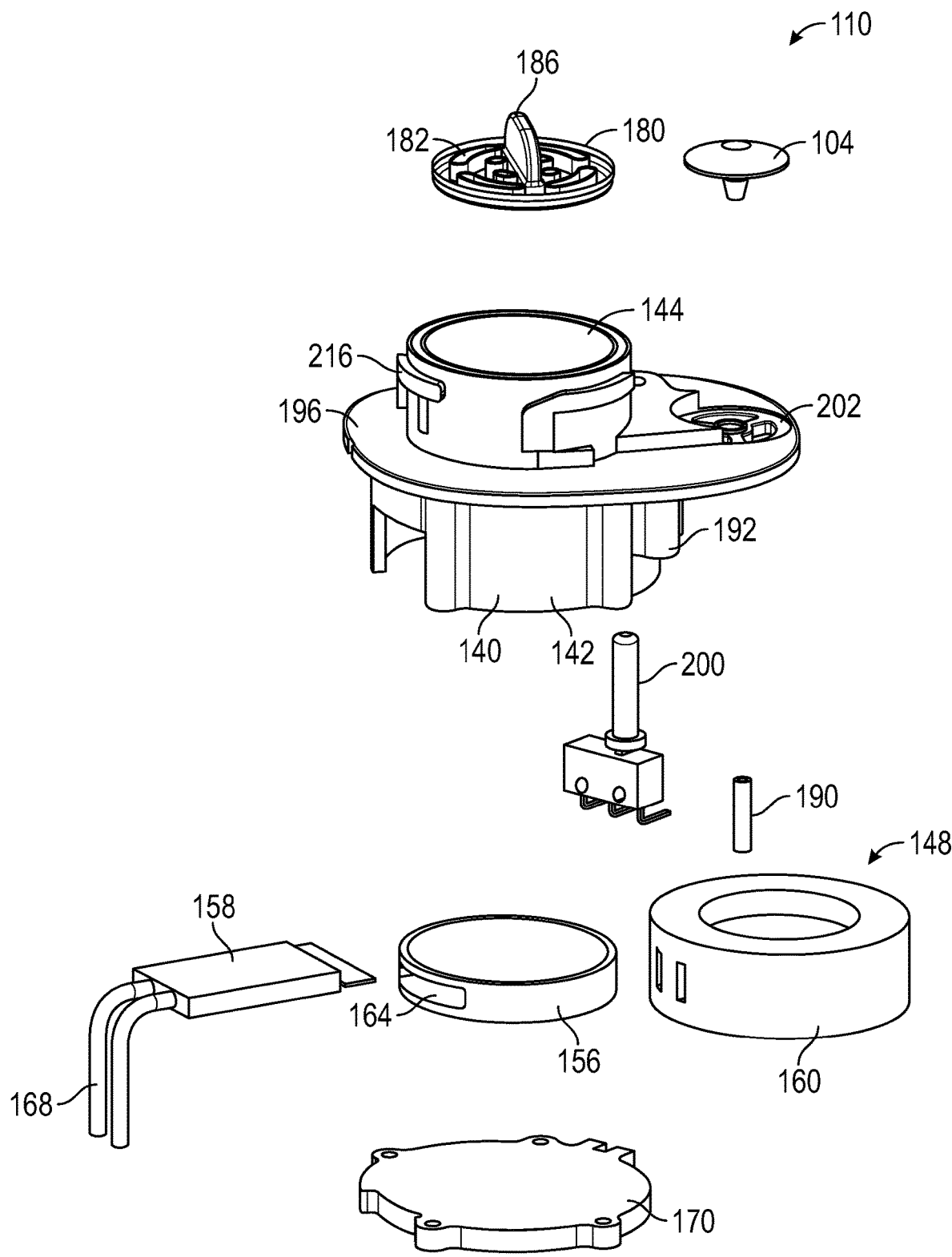
FIG. 4 is an exploded perspective view of FIG. 3.
Figure 5:
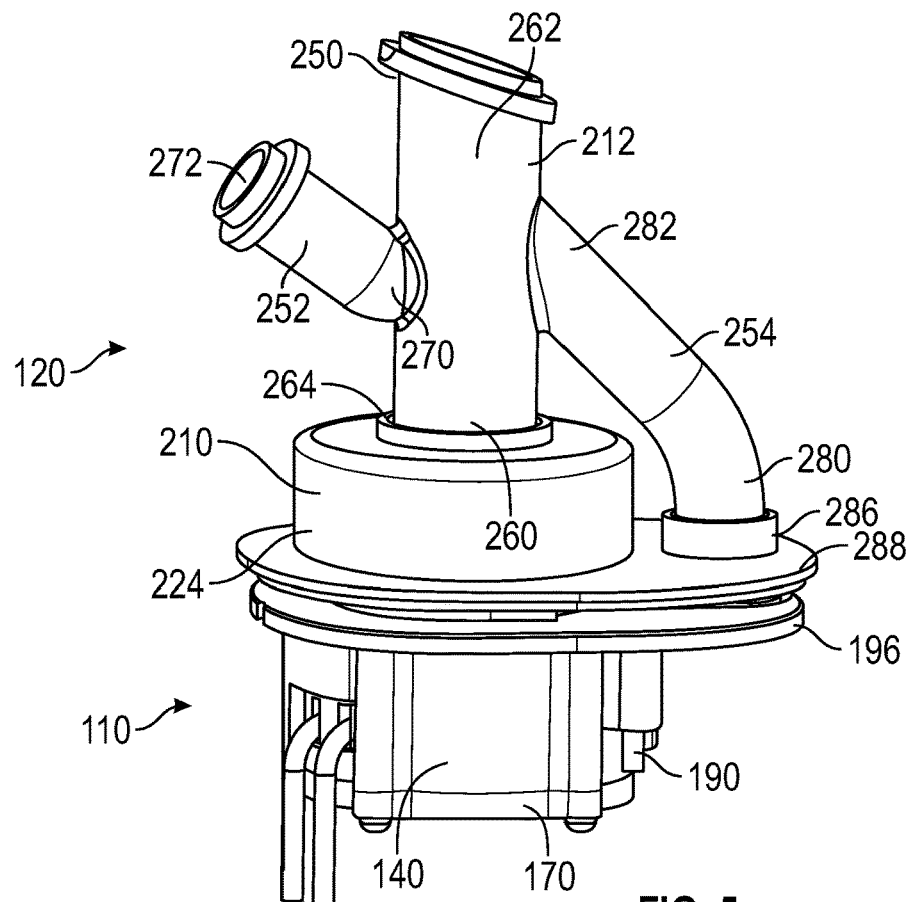
FIG. 5 is a perspective view of a fitting and an upper steam chamber housing of the upper housing assembly mounted to the lower steam chamber assembly.
Figure 6:
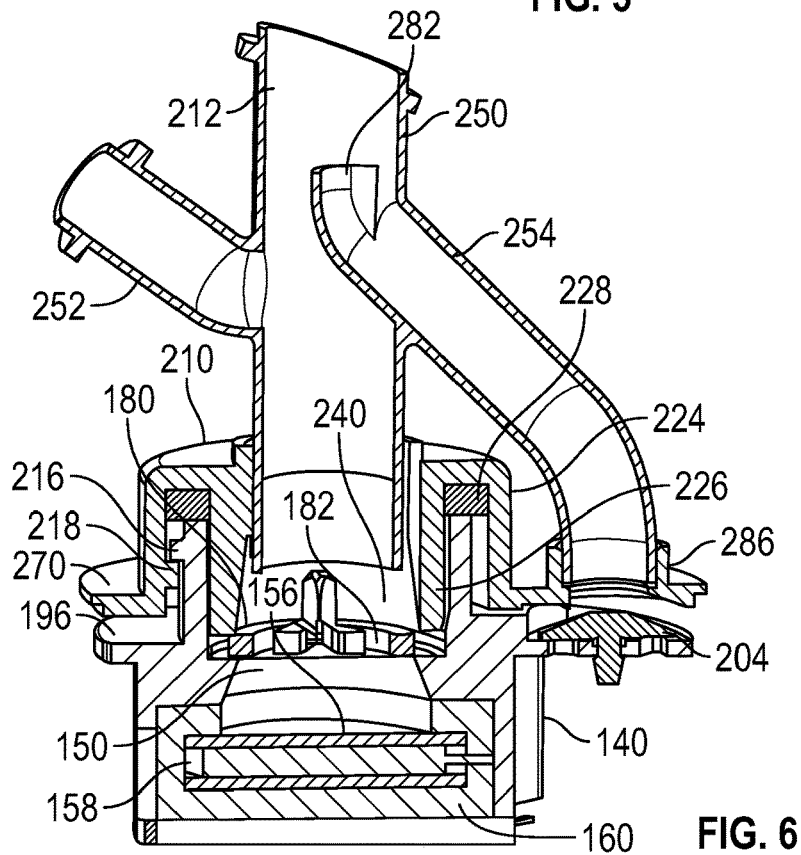
FIG. 6 is a cross-sectional view of FIG. 5.

With reference to FIGS. 2-4, the exemplary lower steam assembly 110 includes a lower steam chamber housing 140 having a lower housing part 142 and an upper housing part 144. The lower housing part 142 has mounted therein a heater assembly 148 and defines a lower steam chamber 150 directly above the heater assembly. Suitable examples of heater assemblies may include, but not be limited to, standard resistance wire, positive temperature coefficient (PTC) or ceramic heater technologies and the like, without departing from the scope of the present disclosure. In the depicted embodiment, the heater assembly 148 includes a heater plate 156, a heating element 158 for heating the heater plate, and a gasket 160. The heater plate 156 is exposed within the lower steam chamber 150 and defines a lower surface of the lower steam chamber. The heating element 158, in the form of a PTC heater, is frictionally secured within a slot or recess 164 defined in the heater plate 156. The heating element 158 is connected through a suitable lead 168 to the power source 116. The gasket 160 surrounds the heating plate 156 and is interposed between the heating plate and an inner wall surface of the lower housing part 142. A bottom plate 170 is secured to the lower housing part 142 to maintain the heater assembly 148 within the lower housing part. In FIG. 6, an inner surface of the lower housing part 142 that defines the lower steam chamber 150 is obliquely oriented relative to the heater plate 156, which ensures that incoming water contacts the heater plate 156 regardless of an upright or relined use position of the steam inhaler 100. For example, at least a portion of the inner surface of the lower housing part 142 can be angled such that water is directly onto the heater plate 156 at any angle of operation of the steam inhaler 100 from vertical to 120 degrees to accommodate a user in a reclined position. In the depicted, the inner surface of the lower housing part 142 is shaped such that the lower steam chamber 150 is substantially frustoconical shaped in cross-section.

The lower steam assembly 110 further includes a removable heater barrier 180 provided in the lower steam chamber housing 140 substantially at an interface between the lower and upper housing parts 142, 144. The heater barrier 180 is sized to cover the lower steam chamber 150 and includes steam ports 182 for directing steam from the lower steam chamber 150 of the lower housing part 142 and into the upper housing part, and a gripping member 186. As indicated, the lower and upper housing assemblies 102, 104 are removably coupled to one another, and with the lower housing assembly 102 removed, a user can remove the heater barrier 180 to provide direct access the heater plate 156, allowing the heater plate to be cleaned of any debris or contaminants.

In FIGS. 3 and 4, a water inlet tube 190 is mounted within a receiving boss 192 provided on the lower housing part 142. The inlet tube 190 is in fluid communication with a channel (not visible) defined by the lower housing part 142, the channel delivering water onto the heating plate 170 that is delivered from the water reservoir 106 via the pump 112. A support flange 196 of the lower housing part has mounted thereto a kill switch or pin 200 operable to disconnect power to the heater assembly 148, for example, upon detection of a temperature of the heater assembly that exceeds a predetermined temperature. The support flange 196 further includes a valve seat 202, having fresh air openings, for mounting a valve 202, the operation of the valve to be described hereafter. The support flange 196 is shaped and sized to essentially close off the lower housing assembly 102.

FIGS. 2 and 5-8 depict the upper steam assembly 120 removably mounted to the lower steam assembly 110. The upper steam assembly 120 includes an upper steam chamber housing 210 and a fitting 212 connected to the upper steam chamber housing 210. The upper steam chamber housing 210 is releasably mounted to the lower steam chamber housing 140, for example, by engagement between connectors 216 provided on an outer surface of the upper housing part 142 of the lower steam chamber housing 140 and connectors 218 provided on an inner surface of an outer wall 224 of the upper steam chamber housing 210. Although, it should be appreciated that alternative manners for releasably mounting the lower and upper steam chamber housings are contemplated. The upper steam chamber housing 210 includes an inner wall 226 spaced from the outer wall 224, and an upper seal 228 is fitted within the upper steam chamber housing 210 between the outer and inner walls. In assembly, the upper housing part 142 is fitted between the outer and inner walls 224, 226 and engages the upper seal 228, with the inner wall 226 received in the upper housing part 142. The inner wall 226 defines an upper steam chamber 240 of the upper steam assembly 120. The inner wall 226 is fitted within the upper housing part 144 of the lower steam chamber housing 140 such that the upper steam chamber 240 is in fluid communication with the lower steam chamber 150. It should be appreciated that the steam ports 182 of the heater barrier 180 direct steam from the lower steam chamber 150 into the upper steam chamber 240.

Figure 8:
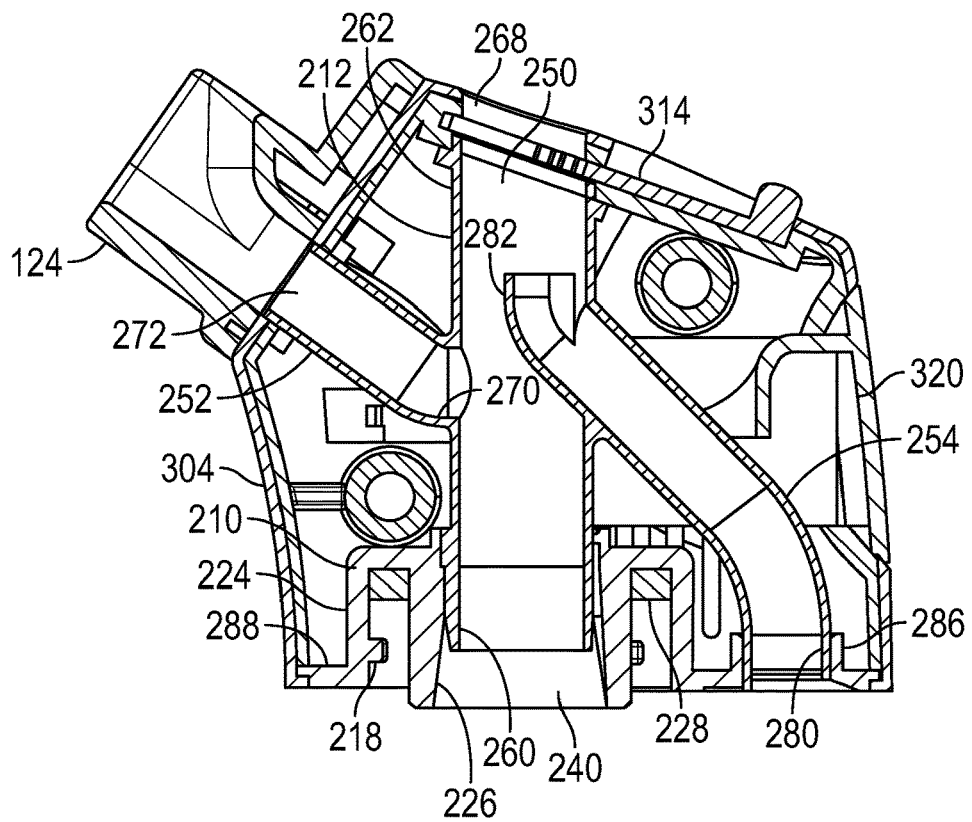
FIGS. 8 and 9 are cross-sectional views of the upper housing assembly.

The fitting 212 is mounted to the upper steam chamber housing 210. According to the present disclosure, the fitting 212 has a steam conduit section 250, a separate nozzle conduit section 252, and a separate fresh air conduit section 254. In the depicted aspect, the fitting 212 is a one-piece, unitary part; although, this is not required, and the conduit sections can be separate components assembled together. The steam conduit section 250 includes an inlet portion 260 and an outlet portion 262. The inlet portion 260 is fitted in an opening 264 in the upper steam chamber housing 210 and is extended from the upper steam chamber 240 to the outlet portion 262 in fluid communication with an exterior vent opening 268. The steam conduit section 250 is shaped to create a straight, linear flow of the steam from the upper steam chamber 240 toward the exterior vent opening 262. The nozzle conduit section 252 includes an inlet portion 270 and an outlet portion 272. The inlet portion 270 is at a location downstream of the upper steam chamber 240 and upstream of the exterior vent opening 262. As shown, the nozzle conduit section 252 is extended obliquely upwardly from the steam conduit section 250 to the outlet portion 272. The outlet portion 272 of the nozzle conduit section 252 is connected to the steam nozzle 124. The fresh air conduit section 254 includes an inlet portion 280 and an outlet portion 282, and is extended obliquely downwardly from the steam conduit section 250. The inlet portion 280 is connected to the upper steam chamber housing 210, for example, by a boss 286 provided on a support flange 288 extended from the upper steam chamber housing 210. The support flange 288 can be shaped similar to the support flange 196, and is shaped and sized to essentially close off the upper housing assembly 104. In assembly, the inlet portion 280 of the fresh air conduit section 254 is aligned with the valve 204 provided on the valve seat 202 of the support flange 196. It should be appreciated that movement of the valve 204 from a closed position to an open position allows fresh air to flow through the openings in the valve seat 202 and into the fresh air conduit section 254. The outlet portion 282 of the fresh air conduit section 254 is provided at least partially within the steam conduit section 250 at a location downstream of the nozzle conduit section 252 and upstream of the exterior vent opening. In FIGS. 6 and 8, the outlet portion 282 of the fresh air conduit section is shaped (for example, coved upward) to inject fresh air in-line with the flow of steam through the steam conduit section, thereby preventing the creation of turbulent flow within the steam conduit section 250. It should be appreciated that the fresh air directed into the fresh air conduit section 254 is air that has a temperature substantially lower than a temperature of the steam generated in the lower steam assembly 110, and the lower temperature or cooler air can be from an exterior of the steam inhaler 100 or from an interior of the steam inhaler.

Therefore, with the exemplary fitting 212, steam flows freely from the lower steam chamber 150 into the upper steam chamber 240, and through the steam conduit section 250 toward the exterior vent opening 268. A suction provided at the steam nozzle 124 redirects the steam into the nozzle conduit section 252, through the steam nozzle and into the mask 126 releasably fitted onto the steam nozzle. With the valve 204 in the open position, fresh air is able to flow into the fresh air conduit which directs additional, cooling fresh air into the steam conduit section 250 to reduce a temperature of the steam exiting the exterior vent opening 268.

As indicated previously, the lower housing assembly 102 includes the housing 108 for housing the blower 114 and the power source 116. The blower 114 is adapted to generate a flow of fresh air within the housing 108. This flow of fresh air can slightly pressurize the interior of the housing 108 moving the valve 204 away from the valve seat 202. However, it should be appreciated that alternative manner for moving the valve to its open position is contemplated. With the valve 204 in the open position fresh air is allowed to flow into the inlet portion 280 of the fresh air conduit section 254. Further, in FIG. 2, the power source 116 is a rechargeable battery mounted in the lower housing assembly 102, and secured between the water reservoir 106 and the lower steam chamber housing 140. An electrical connector 290 (i.e., a DC jack) is provided on the lower housing assembly 102 allowing the steam inhaler 100 to be operated as a corded device as the batteries recharge in the background. A power button 292 for the steam inhaler 100 is further operably mounted to the lower housing assembly 102.

Figure 7:
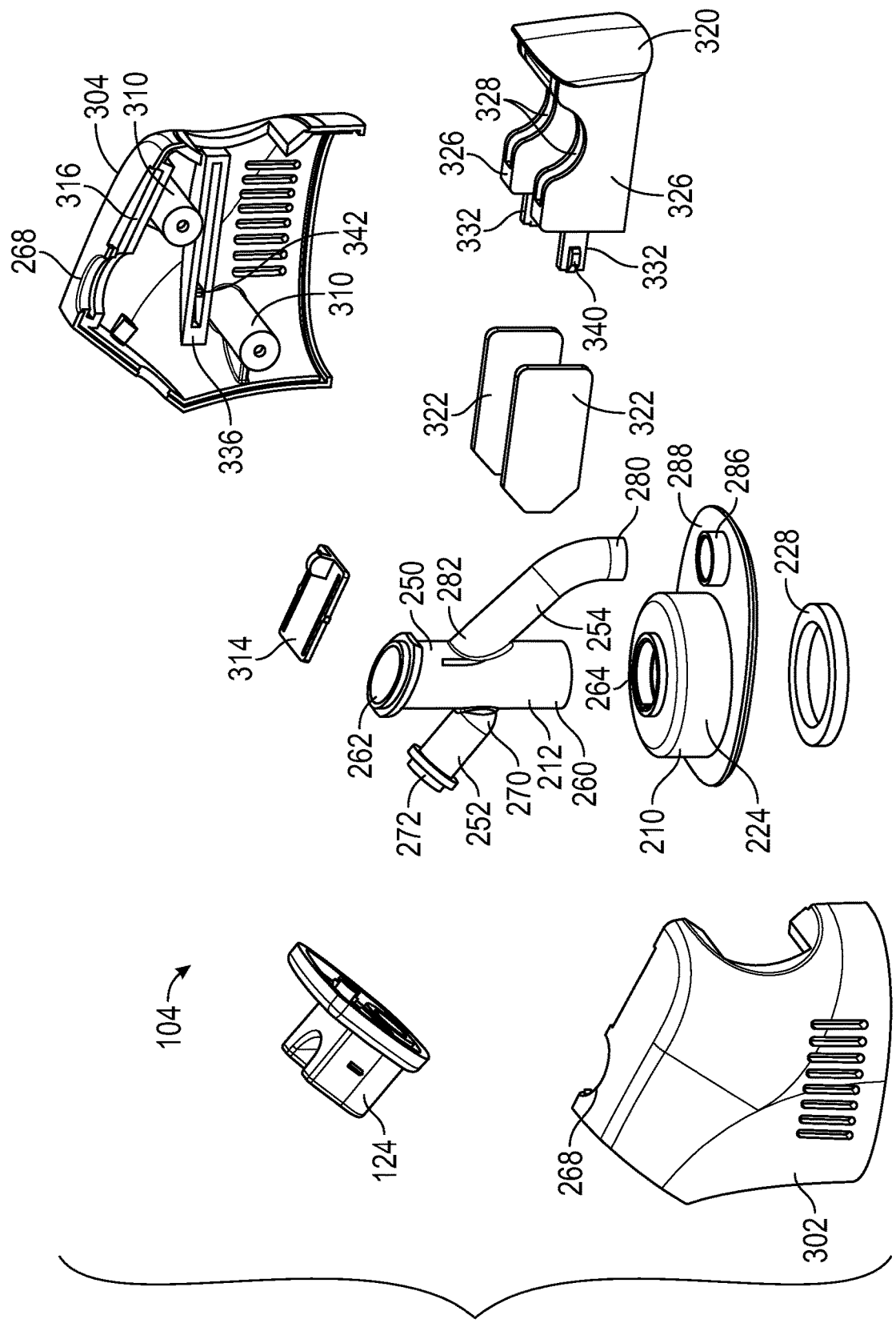
FIG. 7 is an exploded perspective view of the upper housing assembly.
Figure 9:
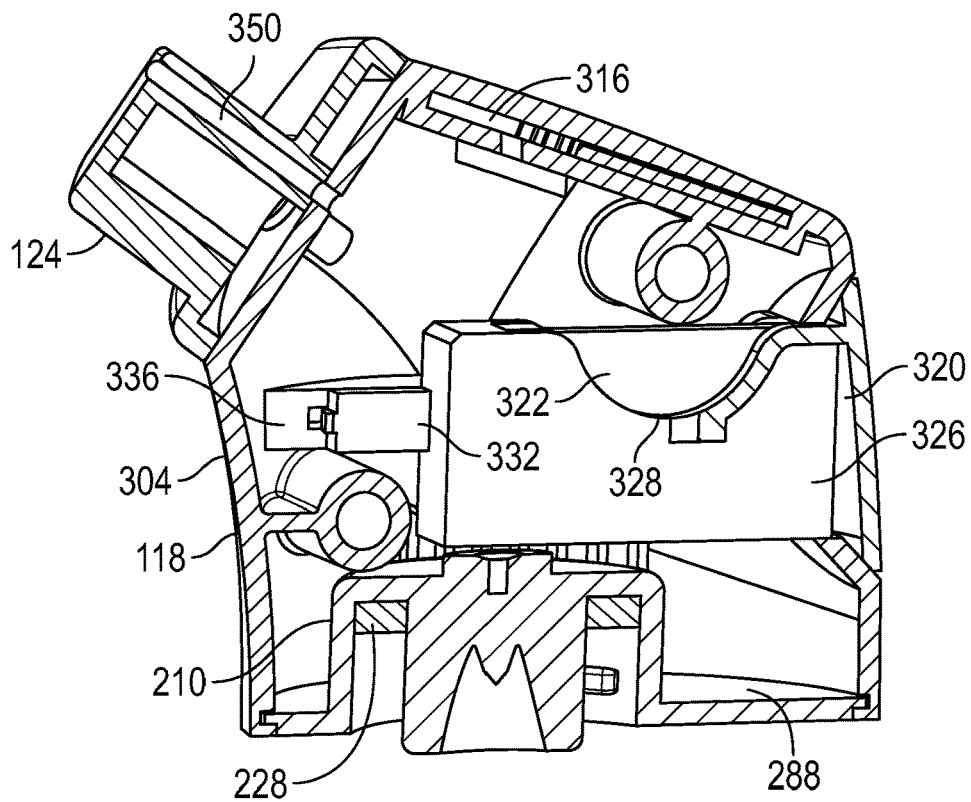
Figure 10:
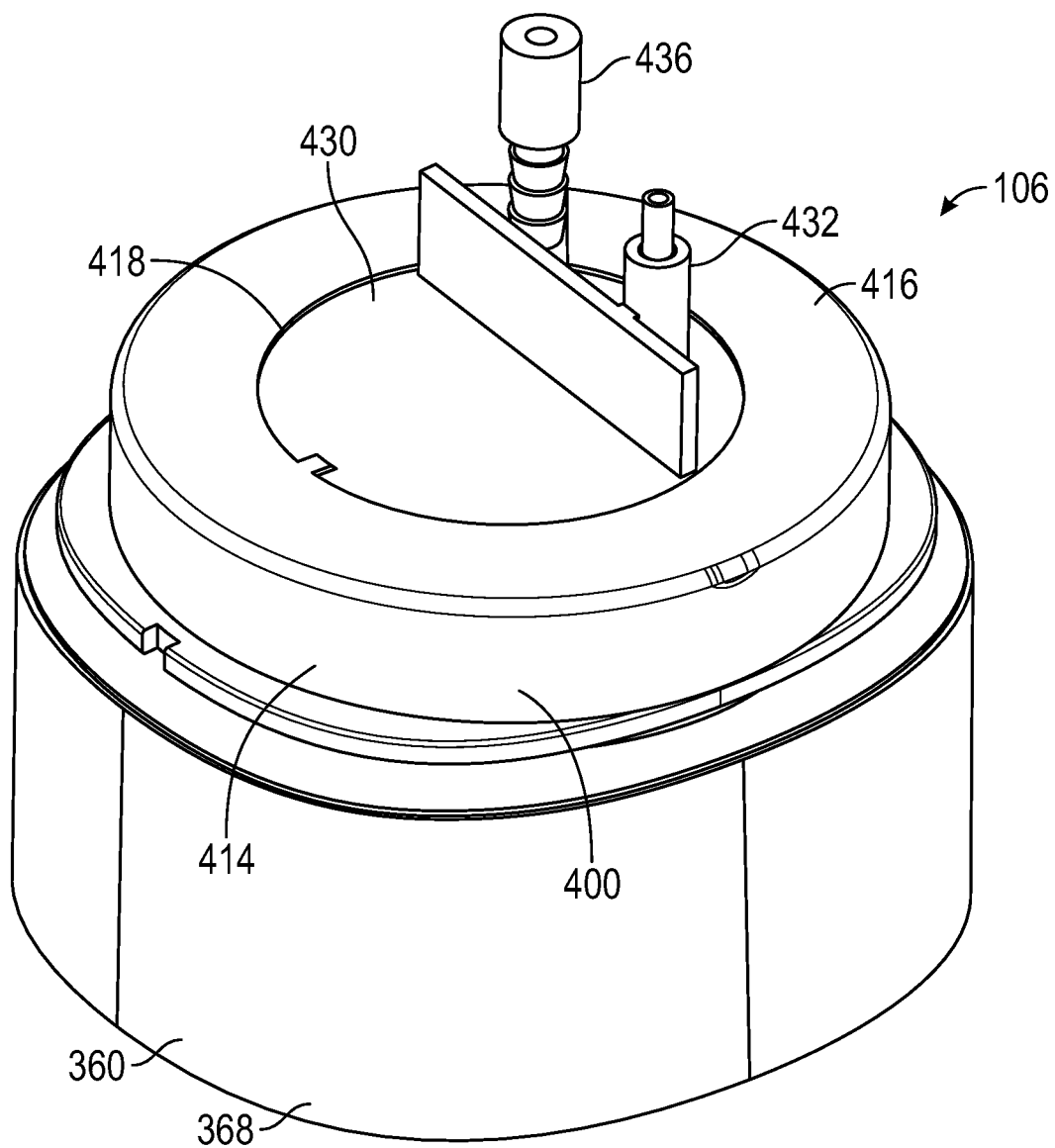
FIG. 10 is a perspective view of the water reservoir.

In FIGS. 7-9, the upper housing assembly 104 includes the housing 118 defined by first and second housing parts 302, 304. The first and second housing parts when connected together, for example, via screws threaded into bosses (only bosses 310 on the second housing part 304 are visible), define the exterior vent opening 268. The steam nozzle 124 is fastened to the housing 118 at the location of the outlet portion 272 of the nozzle conduit section 252. A closure member, for example the depicted slider 314, is movably mounted within a guide 316 defined by the housing 118 between an open position where the exterior vent opening 268 is open and a closed position where the exterior vent opening is closed. This slider 314 can be solid, as shown, or have holes or a geometry to better control the steam and temperature in the facemask area. In addition, the upper housing assembly includes an extendable scented pad drawer 320 configured to releasably hold a scented pad 322 allowing for customized personal scents to the steam flowing into the mask 126. More particularly, the drawer 320 includes a receptacle 326 having an opening 328 sized to receive the scented pad 322. In the depicted aspect, a guide finger 332 extends from the receptacle 236 and is configured to be movably received in a second guide 336 provided on the housing 118. The guide finger 332 can be formed with a bump or protrusion 340 that moves along the second guide 336, and the second guide 336 can be formed with catch 342 which cooperates with the protrusion 340 to maintain the drawer in a closed condition. The drawer can be moved between an open condition where the scented pad 322 can be placed into and out of the receptacle opening 328, and the closed position. To allow scent to mix with the steam flowing into the mask, the steam nozzle 124 includes a bore 350 formed therein for directing scented air from within the housing 118 through the steam nozzle 124 and into the mask 126. In the depicted aspect, the drawer 320 includes a pair of receptacles 326 for a pair of scented pads 322; although this is not required.

With reference to FIGS. 2 and 10-13, the removable water reservoir 106 includes a container 360 having a side wall 362 and a bottom wall 364. The side wall 362 can be an inner side wall with the container 360 having an outer side wall 368. The bottom wall 364 includes a mount for the filter 130. In the depicted aspect, the mount is defined by a stem 366 extended upwardly from the bottom wall 364, and the filter 130 includes a base 370 adapted to accommodate the stem. By way of example, the base 370 can have a cylindrical shaped sleeve 372 extended therefrom for receiving stem. Alternatively, the base can include an opening or bore for receiving the stem. The filter base 370 includes a water permeable top plate 376 and a water permeable bottom plate 378 connected to the top plate. The bottom plate 378 is substantially U-shaped in cross-section so as to define a gap between the top and bottom plates. A first filtration media 382 (e.g., a first sheet of felt, mesh or media with one or more holes) is secured immediately beneath the top plate 376 and a second filtration media 384 (e.g., a second sheet of felt, mesh or media with one or more holes) is secured atop the bottom plate 378. Between the first filtration media 382 and the second filtration media 384, additional filtering media (e.g. a demineralization media) can be added for treating the water flowing through the filter 130. It is understood that different filtering configurations with different combination of media can be used. To secure the filter 130 within the water reservoir 106, the filter is slid onto the stem 366, and feet 388 provided on the bottom plate 378 space the bottom plate 378 from the bottom wall 364. Further, in the present embodiment the base 370 is sized slighter smaller than an inner dimension of the container 360, and the first filtration media 382 extends from the base 370 for engagement with the side wall 362 of the container 360, which substantially prevents water seepage between the side wall 362 and the base 370.

Figure 11:
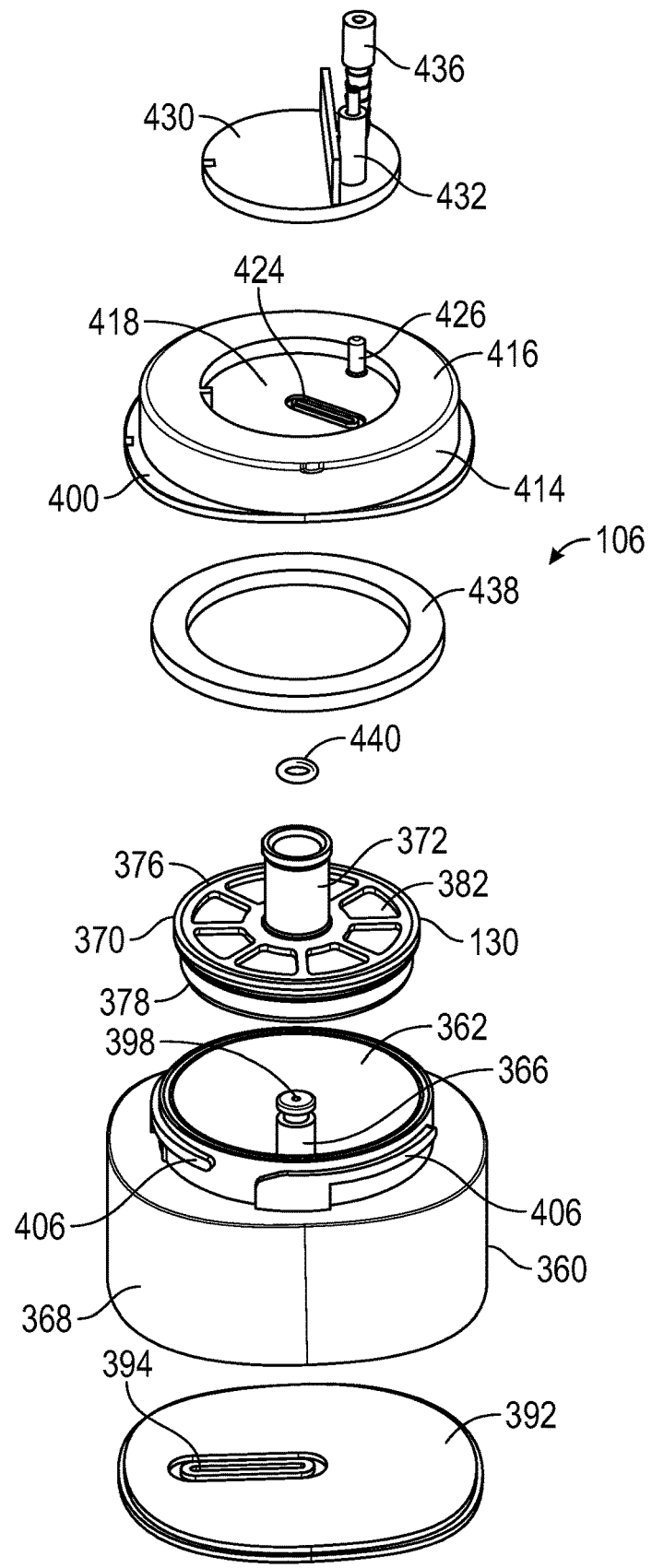
FIG. 11 is an exploded view of FIG. 10.
Figure 12:
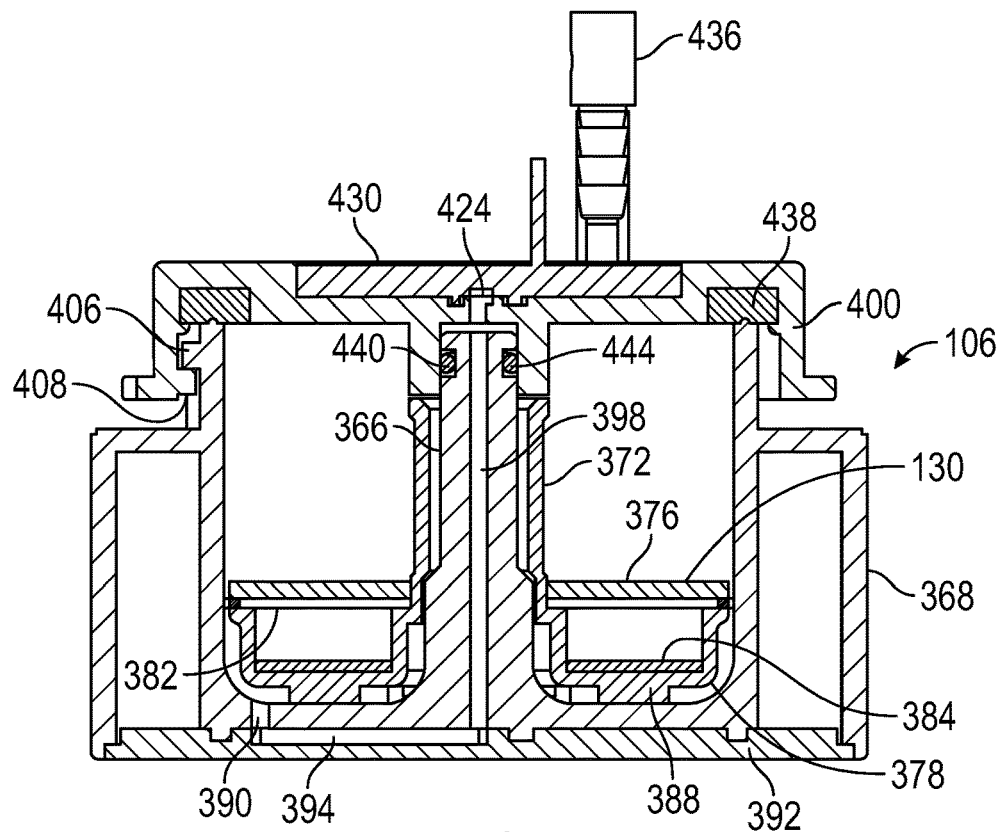
FIGS. 12 and 13 are cross-sectional views of FIG. 10.
Figure 13:
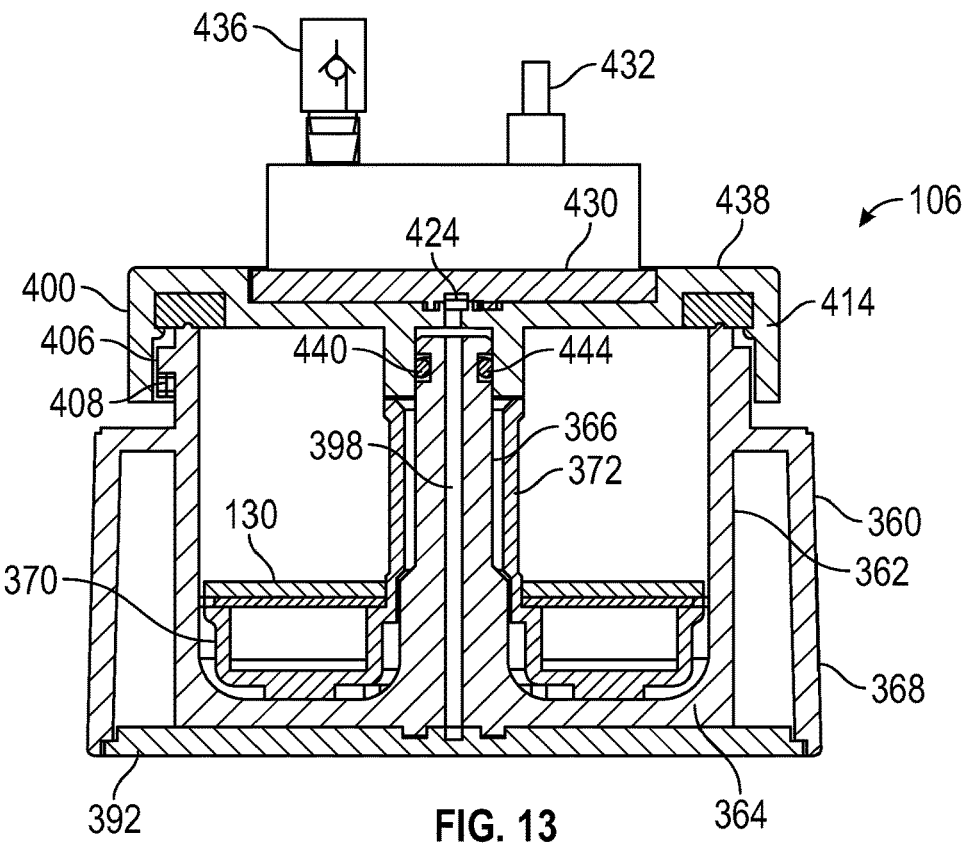

In the depicted aspect of the water reservoir 106, the bottom wall 364 of the container 360 includes a water outlet 390, which is positioned such that any practical orientation during use of the steam inhaler 100 results in any remaining water in the reservoir 106 collecting in the area around the outlet 390, and therefore, accessible to a first water channel 394. A bottom support 392 secured beneath the container 360 includes the first water channel 394 in fluid communication with the outlet 390. The stem 366 includes a second water channel 398 in fluid communication with the first water channel 394. The container 360 is releasably mounted to a cover 400, that is secured and maintained within the lower housing assembly 102, for example, by engagement between connectors 406 provided on an outer surface of the side wall 362 of the container 306 and connectors 408 provided on an inner surface of an outer wall 414 of the cover 40. Although, it should be appreciated that alternative manners for releasably mounting the container 360 and cover 400 are contemplated. A top wall 416 of the cover 400 includes a recessed portion 418 having a third water channel 424 and a first vent tube 426 which allows air to enter the container 360 when water is expelled. The third water channel is in fluid communication with the second water channel 398 of the stem 366. A cap 430 is fitted within the recessed portion 418 to cover the third water channel 424. The cap includes a water outlet conduit or tube 432 in fluid communication with the third water channel 424 and a second vent tube 436 fitted over the first vent tube. Further depicted in FIGS. 11-13 is an upper seal 438 fitted within the cover 400 for engagement with the side wall 362 of the container 360 and a seal ring 440 mounted on the stem 366 for engagement with an inner surface of a boss 444 depending from the top wall 416 of the cover.

In use, with the filter 130 properly positioned within the container 360, water poured into the container initially flows through the filter to fill the gap between the filter base 370 and the bottom wall 364 of the container 360. The pump 112 mounted within the lower housing assembly 102 is adapted to pressurize the water reservoir 106 to deliver filtered water from the water reservoir to the lower steam chamber 150. Upon pressurization of the container 360 via the pump 112, filtered water is forced to flow through the water outlet 390, through the first water channel 394, through the second water channel 398, through the third water channel 424 and into the outlet tube 432. The outlet tube 432 is fluidly connected to the pump 112, and the pump is fluidly connected to the inlet tube 190 of the lower steam assembly 110. At least one of the first and second vent tubes 426, 436 can be adapted to open when pressure in the container 360 exceeds a predetermined pressure and/or when the steam inhaler is turned off As is evident from the foregoing, the exemplary steam inhaler 100 is adapted to generate steam by dripping water from the water reservoir 106 onto the heater plate 156 of the heater assembly 148 located in the lower steam chamber 150. The removable water reservoir 106 with the demineralization in-line filter 130 provided therein is located beneath the lower steam assembly 110, and the pump 112 is provided to deliver water droplets to the lower steam chamber 150. The steam inhaler 100 can be corded or cordless, is easy to hold, and because the lower steam chamber 150 is substantially frustoconical shaped in cross-section (see FIG. 6) the steam inhaler 100 can operate from upright to reclined positions, with incoming water maintaining contact with the heater plate 156. The inner wall 226 of the upper steam housing 210 that defines the upper steam chamber 240 can also be tapered relative to the heater plate 156 to further facilitate this feature. The exemplary fitting 212 fluidly connects the lower steam chamber 150 to the mask 126 and the exterior vent opening 268. The exterior vent opening 268 in fluid communication with the fitting 212 is adapted to exhaust steam out of a top of the steam inhaler when a user is not inhaling within the mask. A stream of cooler fresh air is added to steam existing the exterior vent opening 268 via the fresh air conduit section 254 of the fitting 212 to lower the temperature of the steam as it exits the steam inhaler.

With the shape of the fitting 212, when the user wearing the mask 126 inhales the steam diverts into the nozzle conduit section 252 of the fitting 212 and into the mask. However, some portion of the steam flowing through the fitting 212 can be diverted to the mask when a user is not inhaling to create a sense of warmth. This can be predetermined by the part geometry, or adjustable, through means such as the sliding cover 314. The geometry of the fitting 212 is such that it allows the steam to vent freely out the exterior vent opening 268. The Y-connection to the nozzle conduit section 252 comes from the side which allows steam to naturally bypass the inlet portion 270 of the nozzle conduit section 252 and only enter the inlet portion 270 if there is a lower pressure (i.e. suction) created when the user inhales.

It should be appreciated that the above steam diversion technique provided by the fitting 212 can prevent burning of a user's face with steam. In addition, to prevent excessive temperatures at the exterior vent opening 268 which may burn a user's hand if they inadvertently put their hand too close to the exterior vent opening 268, a stream of cooler fresh air is added to the vent output to lower the temperature of the steam as it exits the steam inhaler 100. The outlet portion 282 of the fresh air conduit section 254 of the fitting 212 is adapted to inject the fresh air "in-line" with the flow of the exiting steam (i.e. aligned with the vent axis). The in-line injection of fresh air prevents any obstruction to the steam or turbulence created by the fresh air at the injection point which can block the steam and send it into the mask 126. This cooler fresh air can also be directed to provide cooling to internal components in the steam inhaler 100 to maintain appropriate and safe operating temperatures. The slider 314 allows the user to completely close the exterior vent opening 268 so that all the steam is diverted out the mask.

In addition, because minerals from tap water can cause mineral build-up on the heater plate 156, the present steam inhaler 100 provides the filter 130 in the removable water reservoir 106. As indicated above, the lower steam chamber 150 is appropriately shaped (e.g., substantially frustoconical shaped in cross-section) to enable use of the steam inhaler 100 in any position (i.e., an upright to reclined position) by ensuring that the water will remain in contact with heater plate 156 when the steam inhaler 100 is horizontal or vertical. The steam inhaler 100 is further designed such that the upper housing assembly 104 can separate from the lower housing assembly 102 to allow access to the lower steam chamber 150 and heater assembly 148 (via the removable heater barrier 180) for easy cleaning.

It will be appreciated that the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A steam inhaler comprising:
   a steam chamber housing having mounted therein a heater assembly, the steam chamber housing defining a steam chamber directly above the heater assembly, the steam chamber adapted to receive water;
   a fitting mounted to the steam chamber housing, the fitting having a steam conduit section extended from the steam chamber to an exterior vent opening, a nozzle conduit section extended from the steam conduit section at a location downstream of the steam chamber, and a fresh air conduit section extended from the steam conduit section at a location downstream of the nozzle conduit section, and a steam nozzle in communication with the nozzle conduit section for directing steam into a mask releasably fitted onto the steam nozzle, wherein the fitting is configured such that steam flows freely from the steam chamber, through the steam conduit section toward the exterior vent opening, and at least a portion of steam is redirected to the nozzle conduit section by suction at the steam nozzle, and the fresh air conduit directs fresh air into the steam conduit section to reduce a temperature of the steam exiting the exterior vent opening.

2. The steam inhaler of claim 1, wherein an inner surface of the steam chamber housing is obliquely oriented relative to the heater assembly to direct water into contact with the heater assembly.

3. The steam inhaler of claim 1, wherein the fresh air conduit section includes an inlet portion for receiving fresh air and an outlet portion, the outlet portion provided at least partially within the steam conduit section.

4. The steam inhaler of claim 3, wherein the outlet portion of the fresh air conduit section is shaped to inject fresh air in-line with the flow of steam through the steam conduit section.

5. The steam inhaler of claim 3, including a blower for generating a flow of fresh air within the steam inhaler that is directed into the inlet portion of the fresh air conduit section.

6. The steam inhaler of claim 1, including a lower housing assembly provided with the steam chamber housing, and an upper housing assembly removably mounted to the lower housing assembly, the upper housing assembly provided with an upper steam chamber housing defining an upper steam chamber in fluid communication with the steam chamber, and the fitting is mounted to the upper steam chamber housing.

7. The steam inhaler of claim 6, wherein the upper steam chamber housing is releasably mounted to the steam chamber housing.

8. The steam inhaler of claim 6, wherein the upper housing assembly includes an extendable scented pad drawer configured to releasably hold a scented pad, and the nozzle includes a bore formed therein for directing scented air through the steam nozzle and into the mask.

9. The steam inhaler of claim 1, including a removable water reservoir having a filter mounted therein for filtering water to be delivered to a lower steam chamber, and a bottom wall of the water reservoir includes a water outlet in fluid communication with the steam chamber.

10. The steam inhaler of claim 9, including a pump adapted to pressurize the water reservoir to deliver filtered water from the water reservoir to the steam chamber.

11. The steam inhaler of claim 10, wherein the water reservoir includes a stem having a water channel formed therein that is in fluid communication with the water outlet, the filter is mounted on the stem, and a separate cover for the water reservoir includes a water outlet conduit in fluid communication with the water channel.

12. The steam inhaler of claim 9, including a rechargeable battery secured between the water reservoir and the steam chamber housing.

13. The steam inhaler of claim 1, including a closure member movable between an open position where the exterior vent opening is open and a closed position where the exterior vent opening is closed.

14. A steam inhaler comprising:
a lower housing assembly including:
a lower steam chamber housing having mounted therein a heater assembly, the lower steam chamber housing defining a lower steam chamber directly above the heater assembly;
an upper housing assembly including:
an upper steam chamber housing releasably mounted to the lower steam chamber housing, the connection of the upper steam chamber housing to the lower steam chamber housing allowing for the removal of the upper housing assembly from the lower housing assembly,
a fitting mounted to the upper steam chamber housing, the fitting having a steam conduit section in communication with the lower steam chamber and an exterior vent opening, a nozzle conduit section extended from the steam conduit section and in communication with a steam nozzle, and a fresh air conduit section extended from the steam conduit section at a location downstream of the nozzle conduit section and in communication with an interior of the lower housing assembly, and
a mask releasably fitted onto the steam nozzle,
wherein the fitting is configured such that steam flows freely from the lower steam chamber through the steam conduit section toward the exterior vent opening, and at least a portion of steam is redirected to the steam nozzle conduit section by suction at the steam nozzle, and the fresh air conduit directs fresh air into the steam conduit section to reduce a temperature of the steam exiting the exterior vent opening; and
a water reservoir removably mounted to the lower housing assembly, the water reservoir having a filter for filtering water to be delivered to the lower steam chamber.

15. The steam inhaler of claim 14, wherein the upper housing assembly includes an extendable scented pad drawer configured to releasably hold a scented pad, and the steam nozzle includes a bore formed therein for directing scented air through the steam nozzle and into the mask.

16. The steam inhaler of claim 14, wherein a pump is mounted within the lower housing assembly, the pump is adapted to pressurize the water reservoir to deliver filtered water from the water reservoir to the lower steam chamber.

17. The steam inhaler of claim 14, wherein the water reservoir is releasably mounted to a cover provided in the lower housing assembly, the cover has a water outlet conduit in fluid communication with the lower steam chamber.

18. The steam inhaler of claim 14, wherein an outlet portion of the fresh air conduit section is shaped to inject fresh air in-line with the flow of steam through the steam conduit section.

19. The steam inhaler of claim 14, wherein the lower housing assembly includes a blower for generating a flow of fresh air within the lower housing assembly, and further including a valve member adapted to allow the fresh air to flow into an inlet portion of the fresh air conduit section.

* * * * *